US008734412B1

United States Patent
Pacelli (10) Patent No.: US 8,734,412 B1
(45) Date of Patent: May 27, 2014

(54) STOMA PROTECTION APPARATUS (76) Inventors: Antonio Pacelli, Totowa, NJ (US);
Franco Pacelli, legal representative, Totowa, NJ (US)

(*) Notice: Subject to any disclaimer, the term of this patent is extended or adjusted under 35 U.S.C. 154(b) by 12 days.

(21) Appl. No.: 13/411,589

(22) Filed: Mar. 4, 2012

Related U.S. Application Data (60) Provisional application No. 61/464,732, filed on Mar. 8, 2011.

(51) Int. Cl.
*A61F 5/44* (2006.01)

(52) U.S. Cl.
USPC .......................... 604/345; 604/337

(58) Field of Classification Search
USPC .......................... 604/337, 345, 347
See application file for complete search history.

(56) References Cited

U.S. PATENT DOCUMENTS

| | | | |
|---|---|---|---|
| 1,922,763 A | 8/1933 | Gricks | |
| 2,549,348 A | 4/1951 | Wagner | |
| 2,656,838 A | 10/1953 | McConnell | |
| 3,421,505 A * | 1/1969 | Freeman et al. | 604/345 |
| 4,917,692 A * | 4/1990 | Steer et al. | 604/355 |
| 5,178,614 A * | 1/1993 | McDowell et al. | 604/332 |
| 5,653,701 A * | 8/1997 | Millman | 604/345 |
| 2001/0020156 A1 * | 9/2001 | Whiteside | 604/342 |
| 2005/0256621 A1 | 11/2005 | Lange | |
| 2009/0182191 A1 * | 7/2009 | Redlich | 600/32 |
| 2009/0216208 A1 * | 8/2009 | Leisner | 604/344 |

* cited by examiner

*Primary Examiner* — Susan Su
*Assistant Examiner* — Guy K Townsend
(74) *Attorney, Agent, or Firm* — W. Patrick Quast (57) ABSTRACT

A stoma protection apparatus is disclosed, comprising a stoma collection bag having an elastomeric protector secured on its exterior surface directly opposite the opening in the interior surface of the bag for connection to the stoma. The structure and placement of the protector in relation to the opening prevent accidental closure of the bag opening to the stoma or compression of the bag when a user connects a belt to his or her waist area, so as to provide an adequate drainage area within the bag. Additionally, elastomeric protectors can be user affixed to a variety of available stoma bags for assured stoma pressure relief protection in an acceptably comfortable manner for the user.

13 Claims, 7 Drawing Sheets

STOMA PROTECTION APPARATUS

CROSS-REFERENCE TO RELATED APPLICATIONS

This application claims the benefit of U.S. Provisional Application Ser. No. 61/464,732, filed Mar. 8, 2011, the entirety of which application is herein incorporated by reference.

FIELD OF THE INVENTION

This invention relates to an improved collection bag following an ostomy procedure, and in particular to an apparatus and method for protecting the resulting stoma in a manner enhancing the security and comfort of the patient.

BACKGROUND OF THE INVENTION

The words ostomy, urostomy, ileostomy and colostomy, and the images they convey produce dread in many people who know very little about them. An ostomy is a surgical procedure that creates an opening on the abdominal wall for waste products to move out of the body. It is performed when a medical condition is so severe that an ostomy offers a better alternative. The quality of life is usually improved for patients with an ostomy, because their previous medical condition was so debilitating.

To really understand an ostomy, it helps to know a little about the body's anatomy. The gastrointestinal tract begins with the esophagus (the tube connecting the mouth and stomach) and continues through the stomach, small intestine, large intestine (colon), rectum, and anus.

Food is swallowed in the esophagus, mixed and churned in the stomach, and digested and absorbed in the small intestine. The waste leaves the small intestine as liquid. The colon absorbs water from the liquid material and stores the remainder as formed stool until it is passed voluntarily out of the body through the rectum. Liquid waste is directed to the kidneys and then to the bladder, where it is held until discharged through the urethra.

A colostomy indicates that the opening is from the colon. When the colostomy is in the left colon, only a pad may be needed to cover the opening. When the opening is in the right side of the colon, some type of appliance or bag is required. There are various types of colostomies. The physician and surgeon recommend the appropriate one for each patient.

An ileostomy involves bringing the ileum (the last portion of the small intestine) to the abdominal surface. When waste matter reaches the ileum it is liquid, so an appliance is needed to collect it.

A urostomy is a stoma (artificial opening) for the urinary system. A urostomy is made in cases where long-term drainage of urine through the bladder and urethra is not possible, e.g. after extensive surgery or in case of obstruction.

Typically after a stoma is created a plastic collection bag is adhesively connected to the body of the opening via a port in the bag for the collection of various bodily fluids. A valve adjacent the base of the bag provides for convenient emptying of the fluids when required.

Obviously there are many occasions in normal patient activity for this opening in the bag to become blocked, closing the stoma with negative consequences including possible infection. For the patient, simply securing a belt around his or her waste presents a problem, and additional activities including driving a car or traveling on a plane add greater potential difficulties.

Many attempts have been put forward to address this and similar ostomy collection bag problems. For example, U.S. Pat. No. 2,656,838 discloses a colostomy unit comprised of a belt 10 (FIG. 1), a plastic or metal plate 16 (FIG. 3), a shield 26 (FIG. 3), and sponge rubber sealing pad 40 (FIG. 3) and washer 44 (FIG. 3). A colostomy bag 24 (FIG. 1) is attached to this apparatus.

Again, in U.S. Pat. No. 2,549,348 a colostomy pouch and protector is described. A circular ring 28 (FIG. 7) has a diametrically secured bridge 29 (FIG. 7), said bridge having means for slidably securing a belt on the bridge. A colostomy bag 20 (FIG. 1) then connects to the bridge. This arrangement prevents the neck of the bag becoming closed due to the pressure form the wearer's clothing (col. 3, lines 4-7).

In U.S. Pat. No. 1,922,763 a colostomy appliance is disclosed. A metal wire frame 14 (FIG. 2) supports a colostomy bag 10 (FIG. 1) and provides the means for securing an elastic belt 54 (FIG. 5).

A protective shield for a stoma pouch is disclosed in U.S. Pat. No. 5,178,614. In this invention a spring clip 90 (FIG. 1) secures a plastic shell 50 (FIG. 2) to a stoma collection pouch 10 (FIG. 1). In operation, as the collection pouch 10 swelled during filing the spring clip portion 90 flexes to allow widening of space 100 between the shell portion 50 and the spring clip portion 90 (FIG. 2). The shell portion 50 acts to prevent physical injury to the stoma and the collection pouch 10 (col. 3, lines 54-59).

A protection device for Pacemaker Patients or Stoma Patients is disclosed in U.S. Patent No. 2005/0256621A1. An arc shaped protector 1 (FIG. 1) consisting of a basic body 2 (FIG. 1) and cover 3 for a belt (FIG. 1) protects pressure sensitive, touch-sensitive, or injured parts of the human body when using a belt that is worn on the body. The basic body 2 has two rubber-like coated bearing surfaces 21 (FIG. 1) to transfer belt stress to the protector.

Additionally, U.S. Patent No. 2009/0182191A1 discloses a stoma protection cap. The Stoma Protective Cap For Protection of the Stoma, encompasses a plate (4) which has a curvature (3) which curvature (3) is formed such that it spans a cavity across the stoma and the plate encompasses at least one retaining region (1) which enables a fastening on clothing so that the plate can be securely held between the clothing and the body.

While the above noted devices and methods provide useful approaches to the problems associated with stoma protection, they do not envision the comfort, simplicity, and economy of the present invention, whether viewed as a virtually universal adjunct to a stoma pouch, or as a complete stoma protection apparatus.

It is therefore a primary object of the invention to provide a combination stoma collection bag and stoma protection device.

An additional object is to provide a pressure minimizing stoma protection device.

A further object is to provide an economically fabricated stoma protection device.

Still another object is to provide stoma protection device that can be employed on a variety of commercially available ostomy collection bags.

Yet another object is to provide a conveniently user applied stoma protection device to an ostomy collection bag.

Another object is to provide a peel-away adhesive backed stoma protection device for fast, convenient user application to an ostomy collection bag as required.

SUMMARY OF THE INVENTION

These and other objects are obtained with the stoma protection apparatus of the present invention.

Users of ostomy collection bags, as, for example, an ileostomy collection bag, are well aware of the limitations of this vitally necessary medical device, and have usually been advised as to the variety of equipment options. Complex and expensive equipment is available for users contemplating vigorous body movements common to activities such as athletics. Typically, however, the user is living a relatively sedentary life. Under these conditions a simple, relatively inexpensive collection bag comprised of a plastic pouch, with a port opening for connection to the stoma, and a peel-away adhesively backed rear area, associated with a rigid flange, for securing the pouch to the abdominal surface, is sufficient. Problems do arise, however, in ordinary daily activity when a belt is secured over the pouch. A user can easily inadvertently close off the opening to the pouch, resulting in unpleasant or even serious consequences.

It occurred that these simple ostomy bags could be significantly improved in reference to ostomy protection if the bag itself prevented accidental port closure.

To this end a stoma protection device has been fabricated in the form of a resilient member and particularly an elastomeric protector for direct connection to the exterior surface of a collection bag. In the preferred embodiment, the resilient member is generally horseshoe in shape, dimensioned so as to enclose a portion of the top and left and right sides of the exterior surface of the bag, enveloping the port to the stoma. The elastomeric protector can be constructed in natural rubber or suitable synthetic elastomers having sufficient elasticity so as to absorb the force of a belt tightened over this area, thereby minimizing pressure to the stoma, and generally providing acceptable comfort to the user. The horseshoe-like shape further provides a protected raised area to accommodate potential fluid build-up within the bag.

In one version of the elastomeric protector a flanged-backed horseshoe-like shape has a raised, arcuate top surface along its complete length. In another version a planar horseshoe shape, that is, without a flange, has a closed annular region comprised of a raised arcuate rib substantially throughout its length.

In both of the above noted versions of the protective element a user can apply an adhesive to the back of the element and secure it to the exterior or outer surface of the collection bag. Alternatively, the protective element can be supplied to the user with a peel-away adhesive backing for convenient connection to a suitable collection bag.

Additionally it is envisioned that manufacturers of these collection bags will supply their bags with the elastomeric protector pre-attached, or with the protective element formed as part of the bag.

DETAILED DESCRIPTION OF THE PREFERRED EMBODIMENTS

Figure 1:
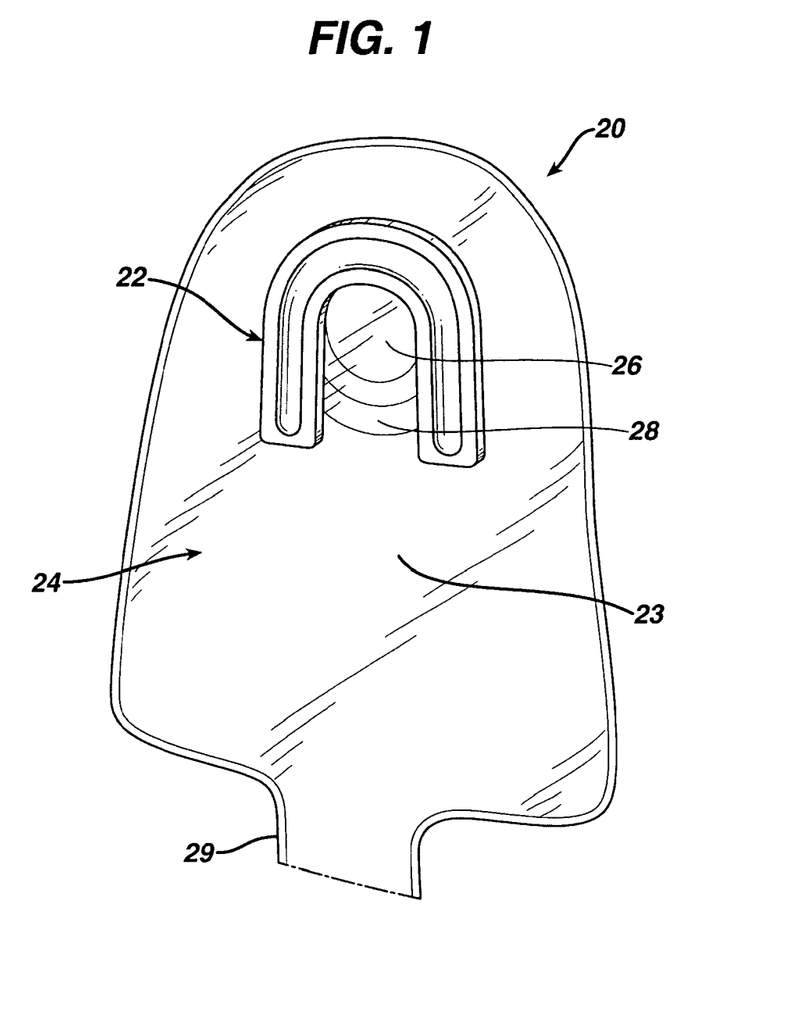
FIG. 1 is a perspective view of one version of the stoma protection apparatus of the invention.
Figure 2:
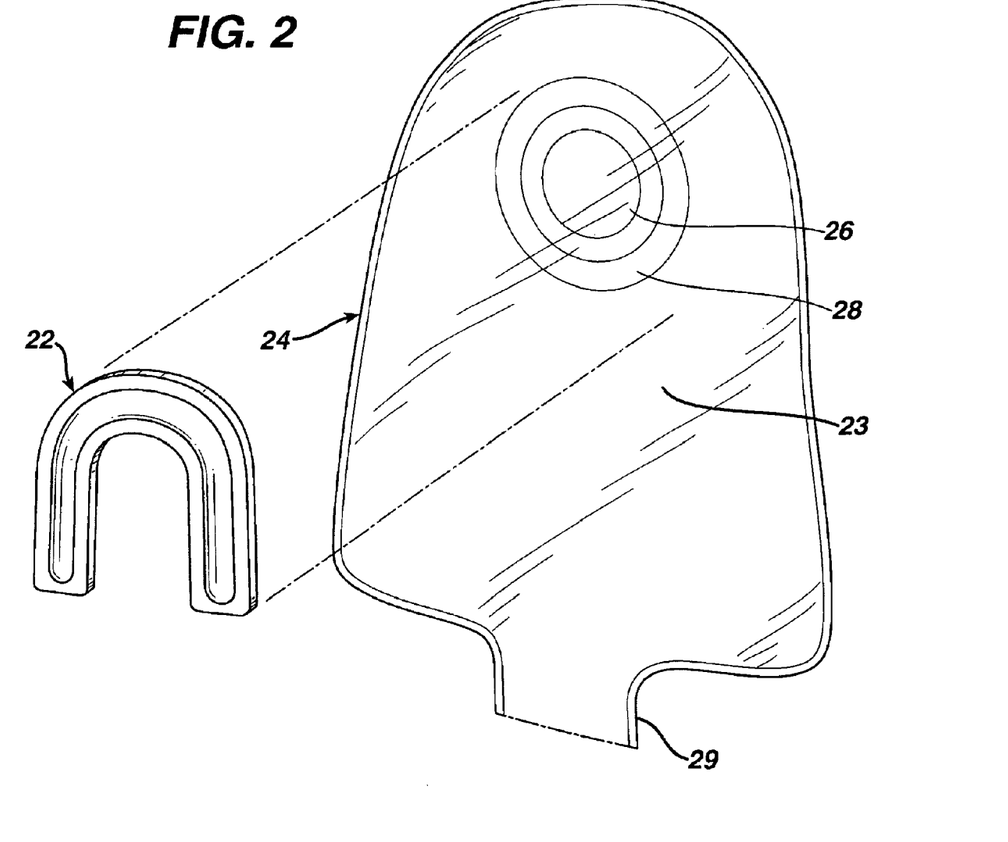
FIG. 2 is an exploded perspective view representing one version of the elastomeric protector and a potential manufacturing method.

Turning now to the drawings wherein similar structures having the same function are denoted with the same numerals, in FIGS. 1 and 2 one version 20 of the stoma protection apparatus is depicted. In this instance one version of the elastomeric protector 22 is shown as pre-affixed to the exterior surface 23 of a stoma bag 24. Typically, a stoma bag is fabricated in clear plastic, having an opening 26 for connection to the stoma; a rigid flange 28 encompassing the opening 26, and a drainage valve (not shown) at the base stem 29 of the bag. The basic stoma collection bag of this type is available from Hollister Incorporated, Libertyville, Ill. 60048U.S.A.

With an elastomeric protector 22 as part of the stoma collection bag 24, the stoma protection apparatus of the invention now precludes compression of the bag 24 by clothing, with or without a belt. Thus the path between the bag opening 26 and the base stem 29 remains open even if a belt is directly secured over it. This allows adequate fluid entry into the bag and with the stoma protected form excess pressure in a comfortable manner for the user.

Figure 3:
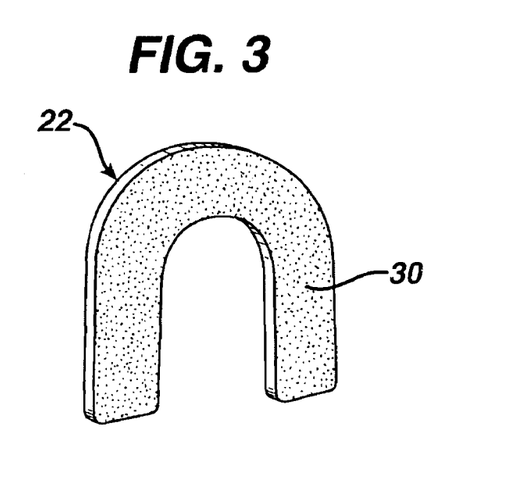
FIG. 3 is a rear perspective view of an elastomeric protector prior to assembly to a stoma bag.

FIG. 3 illustrates one version of an elastomeric protector 22. In this instance a heat sealable adhesive 30 is affixed to the rear surface of the protector. This permits one manufacturing technique for making the protector 22 integral to the bag during the manufacture of the bag such that the bag and protector can be sold as an assembled unit.

Figure 4:
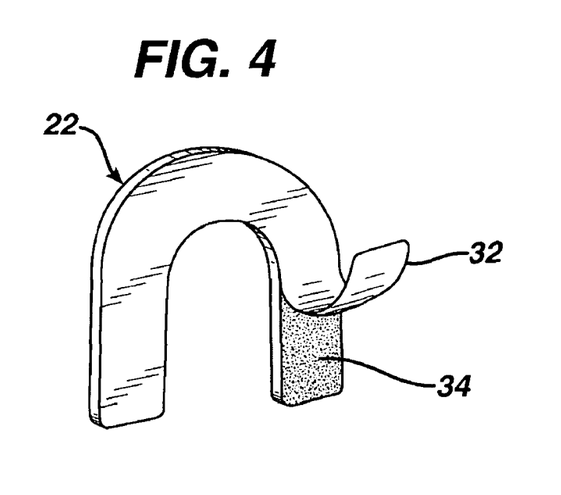
FIG. 4 is rear perspective view of an elastomeric protector having a peel-away adhesive backing for use by the end user.

In FIG. 4 a convenient user method for securing one version of an elastomeric protector 22 to a collection bag is depicted. By simply removing a peel-away adhesive backing cover 32 protecting an adhesive backing 34 on the rear face of the protector, the user can install the protector on the bag which he may have purchased separately. In this case the adhesive backed elastomeric protector could be supplied directly by the manufacturer of the stoma collection bag; or, elastomeric protectors could be purchased directly by users for application to a variety of commercially available stoma bags.

Figure 5:
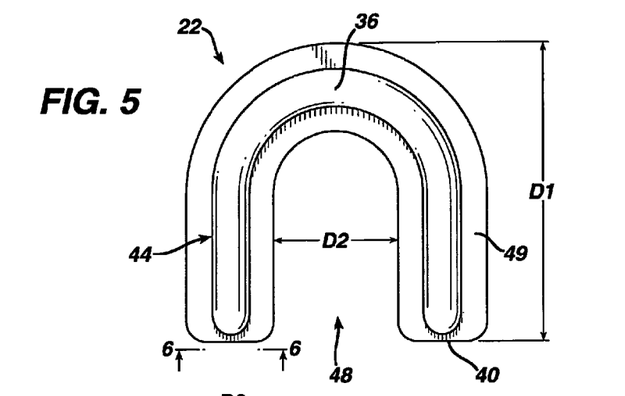
FIG. 5 is an elevational view of one version of the elastomeric protector.
Figures 6, 7:
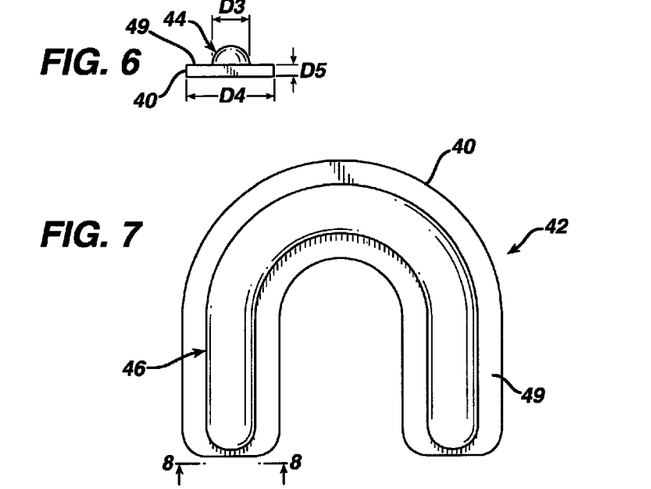
FIG. 6 is an end view of the embodiment of the elastomeric protector of FIG. 5 taken along lines 6-6.
FIG. 7 is an elevational view of an alternative embodiment of the elastomeric protector of FIG. 5.

FIG. 5 and FIG. 6 depict yet another version of the elastomeric protector 22 of the invention. It has a horseshoe-like shape including a semicircular segment 36. The horseshoe-like shape comprises a raised rib 44 arcuate in profile. The rib is surrounded by a planar flange portion 40 defining an opening 48.

Typical dimensions for this elastomeric protector would be 3.00" from the curved top of the horseshoe shape to the base of the flange 40, D1. The width D2, of the center opening 48, is approximately 1.25". The raised rib 44 can measure 0.188" above top surface 49 of the flange 40; and has a width D3 of 0.375". The planar flange itself can measure 0.875" in width, D4; and 0.125" in thickness, D5.

Figure 8:
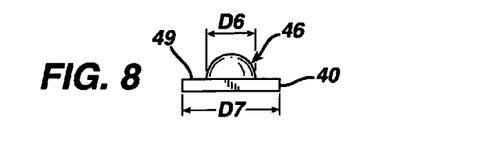
FIG. 8 is an end view elastomeric protector of FIG. 7 taken along lines 8-8.

FIGS. 7 and 8 depict a virtually identical elastomeric protector 42 to that shown in FIGS. 5 and 6 except for a slightly more robust raised rib 46. In this case the raised rib measures approximately 0.250" above the top surface 49 of the flange 40, with a width, D6, of 0.50". Flange 40 is slightly enlarged to 1.00" in width, D7.

Figure 9:
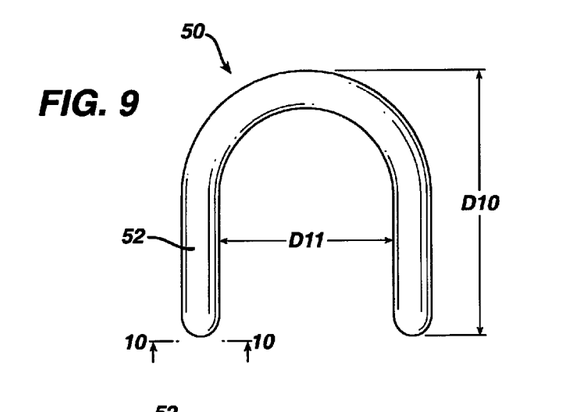
FIG. 9 is an elevational view of yet another version of the elastomeric protector.
Figure 10:
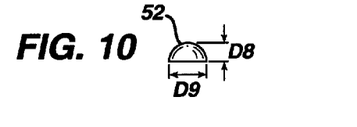
FIG. 10 is an end view of one portion of the elastomeric protector of FIG. 9 taken along lines 10-10.

In FIGS. 9 and 10 a further embodiment of the elastomeric protector 50 is depicted. In effect, the closed annular region shown in FIGS. 5-8 now stands alone as a horseshoe-like shape having a raised, rib profile 52 throughout its length. This version would include a rib height, D8, of 0.188"; and a width, D9, of 0.375". Overall length, D10, typically would be approx. 2.7", with an open area width, D11, of 1.75".

Figure 11A:
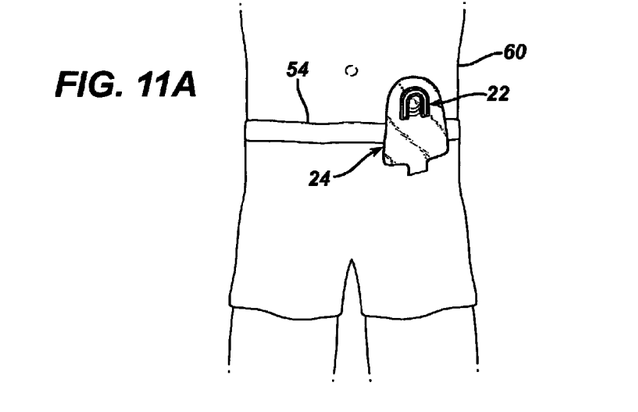
FIG. 11A represents a user with one version of the stoma protection apparatus in place, in an initial stage of dressing.
Figure 11B:
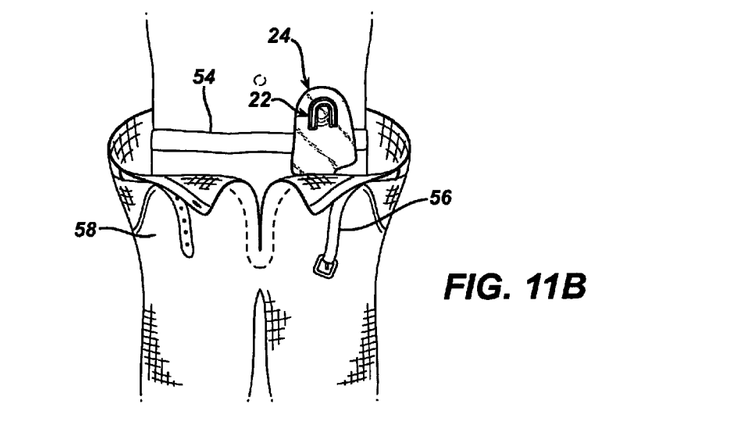
FIG. 11B represents a user applying one version of the stoma protection apparatus immediately prior to employing a belt.
Figure 11C:
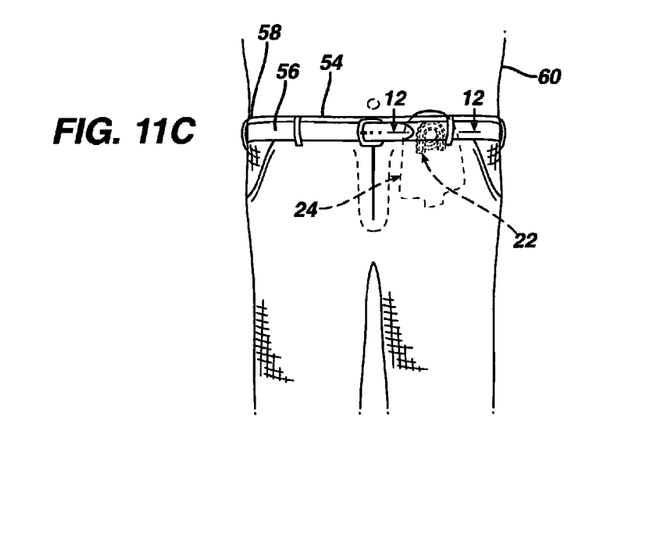
FIG. 11C represents a user having secured a belt over one version of the stoma protection apparatus.
Figure 12:
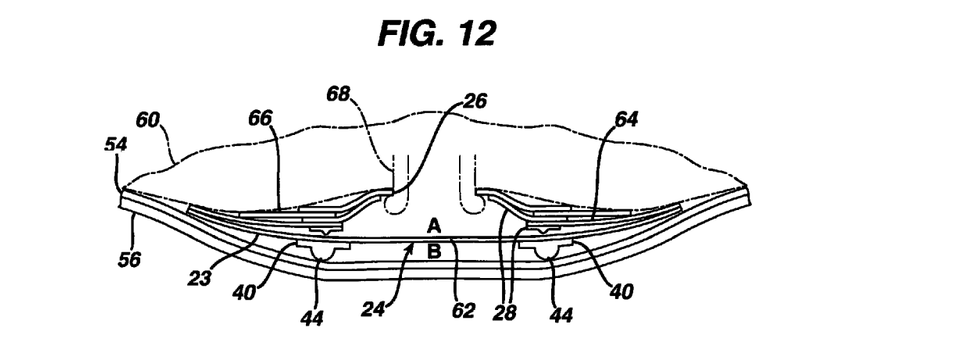
FIG. 12 is a cross-section taken along the line 12-12 of FIG. 11C.

FIGS. 11A-11C represent the steps of a user 60 applying a stoma bag 24, having a pre-attached or built-in elastomeric protector 22, while dressing. The bag is secured to the stoma. The waist band 54 of the user's shorts is typically positioned between the interior side of the bag and the abdomen. Finally the trousers 58 are tightened with a belt 56 positioned directly over the elastomeric protector 22. The semicircular segment 36 of the horseshoe shape and the arcuate profile of rib 44 assist in minimizing the possibility of the bottom side of a belt from hanging up on the top segment of the horseshoe when the user is securing the belt to the waist FIG. 12 is a cross-sectional view taken along the line 12-12 of FIG. 11C. A detailed view is provided of the combination stoma collection bag and stoma protection device of the invention. Denoted region A is the region that receives bodily fluids adjacent the port. This region maintains an open path due to the elastomeric protector 22 and prevents clothing from restricting the flow. Denoted region B allows for additional expansion of an outer layer 62 of the stoma bag 24. The stoma 68 emanating from the user's abdomen is depicted in phantom in contact with the bag opening 26. The rear or interior layer 64 of the bag and the outer layer 62 are maintained in open position even with pressure from clothing 54 and a secured belt 56, due to the presence of the elastomeric protector 22. A soft layer 66 for user comfort is also illustrated.

Thus it can be seen that the stoma protection apparatus of the present invention provides important new security and comfort for user's of ostomy collection bags. The bags can now be supplied with a pre-attached or built-in elastomeric protector, assuring user's of fail-safe stoma protection and comfort during virtually all of their normal daily activities. Additionally, the elastomeric protectors themselves can be obtained for user application at his or her convenience to standard, commercially available stoma bags.

What is claimed is:

1. An improved collection bag for connection to a surgically created opening in a person's anatomy in near vicinity to the person's waistline, the improved bag comprising:
   (a) a bag portion including a base stem end segment and a pouch end, said pouch end having an interior layer and an exterior layer, said exterior layer having an exterior surface, said interior layer to be disposed in substantial juxtaposition to the person's anatomy, said interior layer having an opening, said interior layer opening adapted to connect to the surgically created opening, said exterior layer disposed opposite said interior layer and facing substantially outward in relation to the person's anatomy; and,
   (b) a resilient member forming a part of the said exterior layer and positioned on said exterior surface, said resilient member having a predetermined shape including at least a left side segment and a right side segment, each of said segments having a raised rib portion, each of said left side and right side segments respectively positioned on said exterior surface in a predetermined location encompassing at least a portion of the perimeter of the surgically created opening on at least a portion of the left and right side respectively of the surgically created opening, such that when the collection bag is in place on the user, the predetermined shape of said resilient member is such that no substantial portion of said resilient member is disposed over the surgically created opening, said raised rib portions of said segments providing a protected raised area to accommodate potential fluid build-up within said bag portion.

2. The improved collection bag according to claim 1 wherein said resilient member is a separate item from said bag, said resilient member having means for being secured to said bag by a user.

3. The improved collection bag according to claim 1 wherein said resilient member has a generally horseshoe-like shape including top and left and right side segments dimensioned so as to enclose a top and left and right side of a portion of said exterior layer of said bag enveloping in use said surgically created opening, said horseshoe-like shape providing a protected raised area to accommodate potential fluid build-up within said bag.

4. The improved collection bag according to claim 2 wherein said securing means is an adhesive backing on a rear face of said elastomeric protector with a removable peel-away cover protecting said adhesive, said adhesive backing securing said resilient member to the exterior surface.

5. The improved collection bag according to claim 3 wherein said top segment of said horseshoe-like shape of said resilient member has a semicircular shape.

6. The improved collection bag according to claim 3 wherein said horseshoe-like shape of said resilient member is comprised of a raised, arcuate rib surface throughout its length.

7. The improved collection bag according to claim 6 wherein said resilient member further comprises a planar flange portion completely surrounding said raised, arcuate rib surface.

8. An elastomeric protector for connection to a user selected collection bag, the collection bag having an interior layer and an exterior layer, the exterior layer having an exterior surface, the interior layer having an opening adapted for connection to a surgically created opening in a user's anatomy in near vicinity to a user's waistline, wherein said elastomeric protector includes means for securing said elastomeric protector to the exterior surface of the collection bag, said elastomeric protector having a horseshoe-like shape including at least a left side segment and a right side segment, each of said segments having a raised rib portion, each of said left side and right side segments respectively positioned on the exterior surface in a predetermined location encompassing at least a portion of the perimeter of the surgically created opening on at least a portion of the left and right side respectively of the surgically created opening, such that when the collection bag is in place on the user, the horseshoe-like shape of said elastomeric protector and its position on the exterior surface are such that no substantial portion of said elastomeric protector is disposed over the surgically created opening, said raised rib portions of said segments providing a protected raised area to accommodate potential fluid build-up within the bag portion, said interior layer having an opening, said interior layer opening adapted to connect to the surgically created opening, said exterior layer disposed opposite said interior layer and facing substantially outward in relation to the person's anatomy.

9. An elastomeric protector according to claim 8 wherein said horseshoe-like shape provides a protected raised area to accommodate potential fluid build-up within said bag.

10. An elastomeric protector according to claim 8 wherein said means for securing includes an adhesive backing on a rear face of said elastomeric protector with a removable peel-away cover protecting said adhesive backing, said adhesive backing securing said elastomeric protector to the exterior surface.

11. An elastomeric protector according to claim 9 wherein said horseshoe-like shape of said elastomeric protector is comprised of a raised, arcuate rib surface throughout its length.

12. An elastomeric protector according to claim 11 wherein said elastomeric protector further comprises a planar flange portion completely surrounding said raised, arcuate rib surface.

13. An improved collection bag for connection to a surgically created opening in a person's anatomy in near vicinity to the person's waistline, the improved bag comprising:

(a) a bag portion including a base stem end segment and a pouch end, said pouch end having an interior layer and an exterior layer, said exterior layer having an exterior surface, said interior layer to be disposed in substantial juxtaposition to the person's anatomy, said interior layer having an opening, said interior layer opening adapted to connect to the surgically created opening, said exterior layer disposed opposite said interior layer and facing substantially outward in relation to the person's anatomy; and, (b) a resilient member forming a part of said exterior layer and positioned on the exterior surface, said resilient member creating an elastomeric protector, said elastomeric protector having a generally horseshoe-like shape dimensioned so as to enclose a top and left and right side of a portion of the exterior surface of said bag enveloping in use said surgically created opening such that no substantial portion of said elastomeric protector is disposed over the surgically created opening, said horseshoe-like shape including a raised rib portion area to accommodate potential fluid build-up within said bag.

* * * * *